United States Patent
Tani

(10) Patent No.: US 9,271,944 B2
(45) Date of Patent: Mar. 1, 2016

(54) KETOPROFEN-CONTAINING AQUEOUS ADHESIVE SKIN PATCH

(75) Inventor: Kazuha Tani, Higashikagawa (JP)

(73) Assignee: Teikoku Seiyaku Co., Ltd., Higashikagawa-shi (JP)

(*) Notice: Subject to any disclaimer, the term of this patent is extended or adjusted under 35 U.S.C. 154(b) by 55 days.

(21) Appl. No.: 13/583,940

(22) PCT Filed: Mar. 11, 2011

(86) PCT No.: PCT/JP2011/055728
§ 371 (c)(1),
(2), (4) Date: Sep. 11, 2012

(87) PCT Pub. No.: WO2011/111809
PCT Pub. Date: Sep. 15, 2011

(65) Prior Publication Data
US 2013/0005817 A1    Jan. 3, 2013

(30) Foreign Application Priority Data
Mar. 12, 2010  (JP) ................................. 2010-056098

(51) Int. Cl.
*A61K 9/70*     (2006.01)
*A61K 31/192*   (2006.01)
*A61K 47/10*    (2006.01)

(52) U.S. Cl.
CPC ............ *A61K 9/7061* (2013.01); *A61K 31/192* (2013.01); *A61K 47/10* (2013.01)

(58) Field of Classification Search
None
See application file for complete search history.

(56) References Cited

U.S. PATENT DOCUMENTS

| 4,393,076 A * | 7/1983 | Noda et al. ..................... 424/499 |
| 5,478,567 A | 12/1995 | Nakagawa et al. |
| 2005/0187212 A1 | 8/2005 | Ohki et al. |
| 2010/0029704 A1 | 2/2010 | Hanma et al. |

FOREIGN PATENT DOCUMENTS

| JP | 58-83623 A | 5/1983 |
| JP | 60-155111 A | 8/1985 |
| JP | 61-275212 A | 12/1986 |
| JP | 64-25719 A | 1/1989 |
| JP | 2002-193793 A | 7/2002 |
| JP | 2004-43512 A | 2/2004 |
| JP | 2004-131495 A | 4/2004 |
| WO | WO 93/04677 A1 | 3/1993 |
| WO | WO 2008/093686 A1 | 8/2008 |

OTHER PUBLICATIONS

International Search Report dated Jun. 7, 2011, with English translation.

* cited by examiner

*Primary Examiner* — Sreeni Padmanabhan
*Assistant Examiner* — Jody Karol
(74) *Attorney, Agent, or Firm* — Crowell & Moring LLP

(57) ABSTRACT

Provided is a water-based patch that contains ketoprofen as an active ingredient, provides high transdermal absorbability of the ketoprofen, and has high safety and high storage stability. The water-based patch contains the ketoprofen, an amine, and polyethylene glycol. In the water-based patch, the added amount of the ketoprofen in a paste is 0.1 to 5% by weight, the added amount of the amine in the paste is 0.5 to 10% by weight, and the added amount of the polyethylene glycol in the paste is 5 to 30% by weight. Particularly, in the water-based patch, diisopropanolamine is used as the amine.

3 Claims, 1 Drawing Sheet

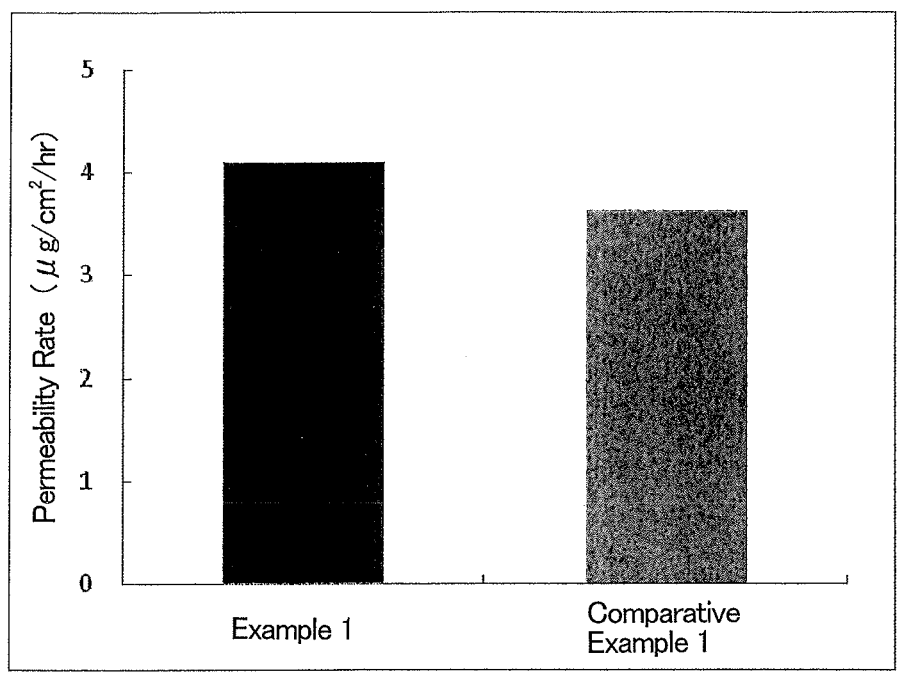

KETOPROFEN-CONTAINING AQUEOUS ADHESIVE SKIN PATCH

TECHNICAL FIELD

The present invention relates to water-based patches containing ketoprofen as an active ingredient, and particularly to a water-based patch that provides high stability and high transdermal absorbability of an active ingredient, that, is, ketoprofen.

BACKGROUND ART

Water-based patches containing, as an active ingredient, ketoprofen that has an anti-inflammatory activity are well known. However, ketoprofen has low water-solubility. Therefore, when a water-based patch contains ketoprofen, a specific solubilizer such as crotamiton, a fatty acid, a fatty acid ester, an essential oil, a polyhydric alcohol, or a surfactant is often used as a solubilizer for the poorly soluble drug (Patent Documents 1 and 2). However, to produce such a patch, some contrivance must be adopted in its production method. Therefore, this production method has a fundamental drawback of low working efficiency during production.

Specifically, many of such specific solubilizers used to solubilize ketoprofen are generally lipophilic solvents. Therefore, such a solvent must be carefully added when a water-based patch is produced. Otherwise, an unfavorable influence may be exerted on the properties of the patch, for example, insolubilization of a water-soluble polymer compound or separation of the lipophilic solvent.

Commonly used water-based patches often contain a polyhydric alcohol such as glycerin at a high concentration. However, when the drug added is ketoprofen that has a carboxylic acid group, an esterification reaction proceeds between the ketoprofen and a solubilizer having a hydroxyl group such as a polyhydric alcohol (for example, glycerin), a lower alcohol, or menthol even at relatively low temperature with a weak acid such as an organic acid or polyacrylic acid, which is a base component of the water-based patch and serves as a catalyst. This results in a problem of low storage stability.

To solve this problem, it is proposed that stabilization of ketoprofen having a carboxylic acid group in its molecule is achieved by dispersing a nonsteroidal anti-inflammatory analgesic containing the ketoprofen in glycerin and glycol having 3 to 30 carbon atoms (Patent Document 3).

However, even in the patch described in this Patent Document, the glycerin used as the base of the water-based patch is an essential ingredient, and therefore it is feared that long-term storage stability will deteriorate due to an esterification reaction. Generally, if a drug is dispersed in a patch, its storage stability is improved, but the drug in the dispersed state results in a reduction in its transdermal absorbability. Therefore, there is a demand for a water-based patch that provides both high storage stability and high transdermal absorbability.

The solubility of ketoprofen in many of patch bases contained in commonly used oil-based patches is high. In addition, many of fatty acid esters, essential oils, crotamiton, etc. used as solubilizers for ketoprofen generally have high compatibility with ketoprofen.

Therefore, an oil-based patch containing ketoprofen provides high transdermal absorbability, and the properties of such an oil-based patch can be maintained without adding a polyhydric alcohol thereto, so that high stability of ketoprofen can be achieved.

Because of the above-described reason, a large number of inventions have been made on oil-based patches containing ketoprofen (Patent Documents 4 and 5), and a large number of products of such oil-based patches have been distributed in the actual pharmaceutical market. However, one problem of the oil-based patches is stimulation to the skin, and it is an object to provide safer products.

PRIOR ART DOCUMENTS

Patent Documents

Patent Document 1: Japanese Patent Application Laid-Open No. Sho58-083623
Patent Document 2: Japanese Patent Application Laid-Open No. Sho61-275212
Patent Document 3: Japanese Patent Application Laid-Open No. 2002-193793
Patent Document 4: International Publication No. WO 93/04677
Patent Document 5: Japanese Patent Application Laid-Open No. 2004-43512

SUMMARY OF THE INVENTION

Problems to be Solved by the Invention

In view of the above circumstances, it is an object of the present invention to provide a patch containing ketoprofen as an active ingredient. The patch provides high transdermal absorbability of ketoprofen and has high safety and high storage stability.

To achieve the above object, the present inventor has made extensive studies and found that a water-based patch that provides high transdermal absorbability of ketoprofen and has high safety and high storage stability can be obtained by selecting an amine which serves as a solvent capable of dissolving a large amount of ketoprofen as a solubilizer for the main drug, and dissolving the ketoprofen in a water-based base containing polyethylene glycol having weak interaction with the ketoprofen. Thus, the invention has been completed.

Means for Solving the Problem

Accordingly, a basic embodiment of the present invention is a water-based patch containing ketoprofen, an amine, and polyethylene glycol.

Specifically, the invention provides a water-based patch wherein the added amount of the ketoprofen in a paste is 0.1 to 5% by weight, the added amount of the amine in the paste is 0.5 to 10% by weight, and the added amount of the polyethylene glycol in the paste is 5 to 30% by weight.

In the most specific embodiment, the invention provides a water-based patch wherein diisopropanolamine is used as the amine.

Effects of the Invention

In the water-based patch provided by the present invention, an amine is selected as the solubilizer for ketoprofen, and the ketoprofen is dissolved in a water-based base containing polyethylene glycol. The ketoprofen can thereby be dissolved stably in the water-based base.

In particular, in the water-based patch provided by the present invention that contains ketoprofen having low solubility in water as an active ingredient, an amine, particularly diisopropanolamine, is used as the solubilizer for the ketoprofen, and the ketoprofen is dissolved in a water-based patch base containing polyethylene glycol having weak interaction with the ketoprofen. The ketoprofen-containing water-based patch can thereby provide high skin permeability, low skin irritability, and high stability of the main drug.

In the ketoprofen-containing water-based patch, a combination of the amine and polyethylene glycol is highly specific. Therefore, the water-based patch provided by the invention provides high transdermal absorbability of ketoprofen and has high safety and high storage stability, which cannot be achieved by conventional water-based patches. Therefore, the advantageous effects of the invention are significant.

BRIEF DESCRIPTION OF DRAWING

FIG. 1 is a graph showing the results of an in vitro rat skin permeation test in Test Example 3.

EMBODIMENTS FOR CARRYING OUT THE INVENTION

As described above, in a basic embodiment, the present invention provides a water-based patch containing ketoprofen, an amine, and polyethylene glycol.

The invention will next be described in more detail.

No particular limitation is imposed on the amount of ketoprofen in the formulation of the water-based patch provided by the invention so long as the formulation can be prepared. Preferably, the added amount of ketoprofen based on the total weight of a paste is 0.1 to 5% by weight. More preferably, the added amount is 0.5 to 2% by weight.

If the amount of ketoprofen in the paste is less than 0.1% by weight, the transdermal absorbability of the ketoprofen becomes insufficient. If the ketoprofen is added in an amount of more than 5% by weight, the amount of the main drug component that has not been absorbed transdermally and remains present in the formulation after the use increases, which is not preferred.

The amine used in the present invention is generally often used as a pH modifier for a base of a water-based patch. However, in the present invention, the amine is added as a solubilizer for poorly soluble ketoprofen.

Examples of the amine used include monoethanolamine, diethanolamine, triethanolamine, diisopropanolamine, and triisopropanolamine. Particularly, diisopropanolamine is preferred.

No particular limitation is imposed on the amount of the amine added to the water-based patch provided by the present invention so long as the formulation can be prepared. The added amount of the amine is preferably in the range of 0.5 to 10% by weight, and more preferably in the range of 1 to 5% by weight based on the total weight of the paste.

If the amount of the amine in the paste is less than 0.5% by weight, the ketoprofen is insufficiently dissolved in the formulation, and this may result in an unfavorable influence such as precipitation of crystals or a reduction in transdermal absorbability.

If the amine is added in an amount of more than 10% by weight, the pH of the formulation increases excessively, and this results in an unfavorable influence on the properties of the formulation, e.g., a reduction in adhesion.

In the present invention, the polyethylene glycol added to the base of the water-based patch functions as an esterification inhibitor for the ketoprofen. The average molecular weight of the polyethylene glycol is preferably 600 or smaller. More specifically, the polyethylene glycol is at least one or two or more selected from the group consisting of polyethylene glycol 200, polyethylene glycol 300, polyethylene glycol 400, and polyethylene glycol 600.

Polyethylene glycols having an average molecular weight of 600 or larger are not preferred, because their melting points are higher than 40° C. and, when one of them is added to the water-based patch of the present invention, a base component such as a water-soluble polymer cannot be dispersed sufficiently, so that an undissolved base component may appear.

No particular limitation is imposed on the added amount of the polyethylene glycol used so long as the formulation can be prepared. The added amount of the polyethylene glycol is preferably in the range of 5 to 30% by weight, and more preferably in the range of 10 to 20% by weight based on the total weight of the paste.

If the amount of the polyethylene glycol in the paste is less than 5% by weight, the stability of the ketoprofen in the formulation is reduced. An amount larger than 30% by weight is not preferred because the properties of the formulation are affected, for example; sagging of the paste occurs after application.

In the water-based patch provided by the present invention, various base components used for commonly used external formulations can be used, so long as such base components exert no additional influence.

No particular limitation is imposed on these base components. Examples of the base components include: commonly used water-soluble polymer compounds such as sodium polyacrylate, polyacrylic acids, carboxyvinyl polymers, carmellose sodium, hydroxypropyl cellulose, polyvinyl alcohol, and gelatin; polyhydric alcohols such as glycerin, propylene glycol, and 1,3-butylene glycol; cross-linking agents such as aluminum hydroxide, potassium aluminum sulfate, and aluminum glycinate; inorganic powders such as kaolin and titanium oxide powders; pH modifiers such as citric acid, sodium edetate, and tartaric acid; surfactants such as polyoxyethylene sorbitan monooleate, sorbitan monooleate, polyoxyethylene monooleate, fatty acid esters of glycerin, fatty acid esters of polyglycerin, fatty acid esters of polyoxyethylene, fatty acid esters of sorbitan, fatty acid esters of polyoxyethylene sorbitan, fatty acid esters of polyoxyethylene sorbitol, polyoxyethylene hydrogenated castor oil, and polyoxyethylene alkyl ethers; preservatives such as methylparaben and propylparaben; and purified water.

If necessary, an absorption promoter, an antioxidant, a flavoring agent, a colorant, etc. may be appropriately added in proper amounts.

Of these components, the water-soluble polymer compound is added to the paste components of the patch in the range of preferably 1 to 30% by weight, and the cross-inking agent is added in the range of preferably 0.01 to 5% by weight. The purified water is added in the range of preferably 10 to 90% by weight, and the inorganic powder is added in the range of preferably 0 to 20% by weight. The added amount of the polyhydric alcohol must be increased or decreased according to the added amount of the polyethylene glycol. Preferably, the total amount added of the polyhydric alcohol and polyethylene glycol is 10 to 50% by weight.

No particular limitation is imposed on the thickness of the water-based patch (paste layer) of the present invention prepared using the above components (excluding the thickness of a backing layer (described later), and the thickness of a film (described later) covering the surface of the patch). The amount of application is sufficiently 150 to 1,000 $g/m^2$ and more preferably 300 to 700 $g/m^2$.

The paste for the water-based patch of the present invention is produced by, for example, mixing the above-described components, then stirring, and aging the mixture by routine methods. The water-based patch of the present invention can be prepared by spreading the obtained paste over a backing layer such as a non-woven fabric, a woven fabric, a sheet, or a film and then, covering the supported paste with a protective film.

Examples of the material of the backing layer used include polyethylene, polypropylene, polyvinyl chloride, polyester, nylon, polyurethane, and rayon. Particularly, if the paste layer is thin, for example, a laminate of a porous or foam of any of the above materials and a woven or non-woven fabric is preferably used.

One of polyethylene, polypropylene, polyester, polyvinyl chloride, and release paper or a laminate thereof can be used as a plastic film covering the surface of the paste. The plastic film used may be subjected to silicone treatment, corona discharge treatment, embossing treatment, plasma treatment, etc.

EXAMPLE

The present invention will next be described in more detail by way of specific Examples, Comparative Examples, and Test Examples. However, the present invention is not limited to these Examples.

Example 1

A hydrated gel was prepared by uniformly mixing 142.5 g of glycerin, 150 g of polyethylene glycol (400), 7.5 g of polyacrylic acid, 40 g of sodium polyacrylate, 40 g of carmellose sodium, 5 g of hydroxypropyl cellulose, 0.6 g of sodium edetate, 0.9 g of dihydroxyaluminum aminoacetate, 1 g of methylparaben, 0.5 g of propylparaben, 15 g of tartaric acid, 200 g of a 20% aqueous polyacrylic acid solution, and a proper amount of purified water.

Next, 10 g of diisopropanolamine and 20 g of ketoprofen dissolved in a proper amount of water were mixed uniformly with the above-prepared gel to obtain a paste for a patch.

The obtained paste was applied to a laminated nonwoven fabric at a paste weight of 500 g/m$^2$, and the adhesive surface was covered with a polyester film. A desired water-based patch was thereby obtained.

Examples 2 to 4

Water-based patches in Examples 2 to 4 were obtained using prescriptions shown in TABLE 1 below by repeating the same procedure as in Example 1.

The prescription used in Example 1 is also shown in Table 1. The added amount of each component is represented by percent by weight. However, in the production in each Example, preparation was performed using amounts (gram) obtained by multiplying the values in the Table by 10.

TABLE 1

| | Examples | | | |
|---|---|---|---|---|
| Ingredients (% by weight) | 1 | 2 | 3 | 4 |
| Ketoprofen | 2 | 2 | 2 | 3 |
| Di-isopropanolamine | 1 | 1 | 1 | 2 |
| Glycerin | 14.25 | 18 | 14.25 | 14.25 |
| Polyethylene glycol (400) | 15 | 10 | — | 15 |
| Polyethylene glycol (600) | — | — | 15 | — |
| Polyacrylic acid | 0.75 | 0.75 | 0.75 | 0.75 |
| Sodium polyacrylate | 4 | 4 | 4 | 4 |
| Carmellose sodium | 4 | 4 | 4 | 4 |
| Hydroxypropyl cellulose | 0.5 | 0.5 | 0.5 | 0.5 |

TABLE 1-continued

| | Examples | | | |
|---|---|---|---|---|
| Ingredients (% by weight) | 1 | 2 | 3 | 4 |
| Sodium edetate | 0.06 | 0.06 | 0.06 | 0.06 |
| Dihydroxyaluminum aminoacetate | 0.09 | 0.09 | 0.09 | 0.09 |
| Methylparaben | 0.1 | 0.1 | 0.1 | 0.1 |
| Propylparaben | 0.05 | 0.05 | 0.05 | 0.05 |
| Tartaric acid | 1.5 | 1.5 | 1.5 | 1.5 |
| 20% Aqueous polyacrylic acid solution | 20 | 20 | 20 | 20 |
| Purified water | q.s. | q.s. | q.s. | q.s. |
| Total | 100 | 100 | 100 | 100 |

Comparative Example 1

In Comparative Example 1, a commercial plaster containing 2% by weight of ketoprofen (thickness of the paste: 143 g/m$^2$) was used.

Comparative Example 2

A hydrated gel was prepared by uniformly mixing 350 g of glycerin, 50 g of polyacrylic acid, 40 g of sodium polyacrylate, 40 g of carmellose sodium, 5 g of hydroxypropyl cellulose, 0.6 g of sodium edetate, 0.9 g of dihydroxyaluminum aminoacetate, 30 g of propylene glycol, 1 g of methylparaben, 0.5 g of propylparaben, 15 g of tartaric acid, 200 g of a 20% aqueous polyacrylic acid solution, 20 g of a 33% aqueous polyvinyl alcohol solution, and a proper amount of purified water.

Next, 20 g of crotamiton and 20 g of ketoprofen dissolved in 40 g of polyethylene glycol (400) were mixed uniformly with the above-prepared gel to obtain a paste for a patch.

The obtained paste was applied to a laminated nonwoven fabric at a paste weight of 500 g/m$^2$, and the adhesive surface was covered with a polyester film. A water-based patch in Comparative Example 2 was thereby obtained.

Comparative Examples 3 and 4

Water-based patches in Comparative Examples 3 and 4 were obtained using prescriptions shown in Table 2 below by repeating the same procedure as in Comparative Example 2.

The prescription used in Comparative Example 2 is also shown in Table 2. The amount of each component is represented by percent by weight. However, in the production in each Comparative Example, preparation was performed using amounts (g) obtained by multiplying the values in the Table by 10.

TABLE 2

| | Comparative Examples | | |
|---|---|---|---|
| Ingredients (% by weight) | 1 | 2 | 3 |
| Ketoprofen | 2 | 2 | 2 |
| Di-isopropanolamine | — | 1 | — |
| Crotamiton | 2 | — | 1 |
| Glycerin | 35 | 35 | 14.25 |
| Polyethylene glycol (400) | 4 | — | 15 |
| Polyacrylic acid | 5 | 5 | 0.75 |
| Sodium polyacrylate | 4 | 4 | 4 |
| Carmellose sodium | 4 | 4 | 4 |
| Hydroxypropyl cellulose | 0.5 | 0.5 | 0.5 |
| Sodium edetate | 0.06 | 0.06 | 0.06 |
| Dihydroxyaluminum aminoacetate | 0.09 | 0.09 | 0.09 |

TABLE 2-continued

|  | Comparative Examples | | |
|---|---|---|---|
| Ingredients (% by weight) | 1 | 2 | 3 |
| Propylene glycol | 3 | — | — |
| Methylparaben | 0.1 | 0.1 | 0.1 |
| Propylparaben | 0.05 | 0.05 | 0.05 |
| Tartaric acid | 1.5 | 1.5 | 1.5 |
| 20% Aqueous polyacrylic acid solution | 20 | 20 | 20 |
| 33% Aqueous Polyvinyl alcohol solution | 2 | — | — |
| Purified water | q.s. | q.s. | q.s. |
| Total | 100 | 100 | 100 |

Test Examples

Test Example 1

Stability Test 1

The patches obtained in Example 1 and Comparative Examples 2 to 4 were packed and sealed in an aluminum bag and stored for one month under the storage condition of 4° C. Then the presence or absence of precipitation of crystals of ketoprofen in each formulation was visually observed. The results are shown in Table 3.

In Table 3, a circle (○) represents a sample with no precipitation of crystals, and a cross (×) represents a sample with precipitation of crystals.

TABLE 3

|  | Example 1 | Comparative Example 2 | Comparative Example 3 | Comparative Example 4 |
|---|---|---|---|---|
| After one-month Storage | ○ | ○ | ○ | × |

Test Example 2

Stability Test 2

The patches obtained in Example 1 and Comparative Examples 2 to 4 were packed and sealed in an aluminum bag and stored for three months under the storage conditions of 40° C. and 75% RH. Then the amount of ketoprofen in each formulation was measured by high-performance liquid chromatography.

The results are shown in Table 4 below.

In these results, an initial amount was set to 100%, and the amount of ketoprofen after storage was represented by percentage.

TABLE 4

|  | Example 1 | Comparative Example 2 | Comparative Example 3 | Comparative Example 4 |
|---|---|---|---|---|
| Initial | 100.0 | 100.0 | 100.0 | 100.0 |
| After three-month Storage | 96.8 | 83.1 | 91.6 | 90.9 |

For each of the patches in Example 1 and Comparative Example 3, the amount of an analog (a glycerin ester of ketoprofen) generated in the formulation under the same conditions as the above storage conditions was measured by high-performance liquid chromatography.

The results are shown in Table 5. The amount of the analog generated was represented by the ratio (%) of the weight of the analog generated to the weight of ketoprofen added.

TABLE 5

|  | Example 1 | Comparative Example 3 |
|---|---|---|
| Initial | 0.02 | 0.02 |
| After three-month Storage | 0.71 | 1.84 |

As can be seen from the results of the stability tests, the patches of the invention were much more excellent in the stability of ketoprofen as compared to the formulations in the Comparative Examples. Particularly, in Comparative Example 3 in which no polyethylene glycol was added, the stability of ketoprofen was low, and the generated amount of the analog of ketoprofen was large.

In the water-based patches in Comparative Examples 2 and 4 in which no amine was added, the stability of ketoprofen was also low. Particularly in Comparative Example 4, crystals were precipitated even under the storage condition of 4° C. Therefore, in the formulation in each Comparative Example, ketoprofen was very unstable in the formulation.

Test Example 3

In Vitro Skin Permeation Test

An in vitro skin permeation test using rat skin was performed on the water-based patch obtained in Example 1 and the commercial plaster containing 2% by weight of ketoprofen in Comparative Example 1.

The dorsal skin excised from a depilated male rat (7 week old Wistar rat) was secured to a vertical permeation test diffusion cell maintained at 37° C. A formulation used as a test object was applied to the stratum corneum side of the excised skin, and 10 mL of phosphate buffered saline (PBS) used as a receiver solution was added to the inner side (dermis side). Then 0.2 mL of the receiver solution was collected at intervals. The permeation amount of ketoprofen was measured by liquid chromatography, and a skin permeation flux was computed from the measured value.

The results are shown in FIG. 1.

Test Example 4

Primary Skin Irritation Test in Rabbits

A primary skin irritation test in rabbits was performed on the water-based patch obtained in Example 1 and the commercial plaster containing 2% by weight of ketoprofen in Comparative Example 1.

One of the formulations was applied to the back of a depilated rabbit and then removed after 24 hours. An irritation index (P. I. I.) was determined from the condition of the skin at 1 hour, 24 hours, and 48 hours after removal.

The evaluation criteria for the irritation index (P. I. I.) are shown in Table 6 below.

TABLE 6

| P.I.I. | Safety Category |
|---|---|
| P.I.I. = 0 | Non-irritant |
| 0 < P.I.I. < 2 | Weak Irritant |

TABLE 6-continued

| P.I.I. | Safety Category |
|---|---|
| 2 ≤ P.I.I. < 5 | Moderate Irritant |
| 5 ≤ P.I.I. | Strong Irritant |

The evaluation results are shown in Table 7 below.

TABLE 7

| Test Formulation | Example 1 | Comparative Example 1 |
|---|---|---|
| Irritation Index (P.I.I.) | 0.04 | 0.08 |

As can be seen from the results shown in FIG. 1 and Table 7, the comparison between the water-based patch of the present invention and the plaster in Comparative Example 1 shows that higher transdermal absorbability and skin irritability are obtained in the water-based patch of the present invention.

As can be concluded from the above results, the water-based patch provided by the present invention is a formulation that provides high transdermal absorbability of ketoprofen and has high safety and high storage stability.

Industrial Applicability

As described above, according to the present invention, a ketoprofen-containing water-based patch that provides high skin absorbability and has low skin irritability and high main drug stability can be provided by using ketoprofen having low water-solubility as an active ingredient and an amine as a solubilizer and dissolving the ketoprofen in a patch base containing polyethylene glycol.

The water-based patch provided by the present invention provides higher transdermal absorbability of ketoprofen and having higher safety and higher storage stability than those of conventional ketoprofen-containing patches, and the medical usefulness of the water-based patch is very high.

The invention claimed is:

1. A water-based patch comprising an adhesive paste comprising
a ketoprofen, an amine as a solubilizing agent for the ketoprofen,
polyethylene glycol as an esterification inhibitor for the ketoprofen,
cross-linking agent, and
polyacrylic acid and/or salt thereof,
wherein the amount of ketoprofen in the adhesive paste is 0.1 to 5% by weight, the amount of the amine in the adhesive paste is 0.5 to 10% by weight, the amount of the polyethylene glycol in the adhesive paste is 5 to 30% by weight, the amount of the cross-linking agent in the adhesive paste is 0.01 to 5% by weight, and the amount of polyacrylic acid and/or salt thereof in the adhesive paste is 1 to 30% by weight,
wherein the adhesive paste is prepared by the steps of: (1) solubilizing the ketoprofen in the amine to form a solubilized ketoprofen, (2) preparing a hydrated gel comprising the polyethylene glycol, cross-linking agent and polyacrylic acid and/or salt thereof in water, and (3) mixing the solubilized ketoprofen into the hydrated gel uniformly to generate a paste.

2. The water-based patch according to claim 1, wherein the amine is diisopropanolamine and the cross-linking agent is dihydroxyaluminum aminoacetate.

3. The water-based patch according to claim 1, wherein diisopropanolamine is used as the amine.

* * * * *